United States Patent [19]

Sach

[11] 4,444,772

[45] Apr. 24, 1984

[54] HISTAMINE H$_1$-ANTAGONISTS

[75] Inventor: George S. Sach, Welwyn, England

[73] Assignee: Smith Kline & French Laboratories Limited, Welwyn Garden City, England

[21] Appl. No.: 391,077

[22] Filed: Jun. 22, 1982

[30] Foreign Application Priority Data

Jun. 27, 1981 [GB] United Kingdom ............... 8119906

[51] Int. Cl.$^3$ ................ C07D 401/14; A61K 31/505
[52] U.S. Cl. .................................... 424/251; 544/320
[58] Field of Search ....................... 544/320; 424/251

[56] References Cited

U.S. PATENT DOCUMENTS

| 4,154,834 | 5/1979 | Brown et al. | 424/251 |
| 4,216,318 | 8/1980 | Brown et al. | 544/310 |
| 4,255,428 | 3/1981 | Brown et al. | 424/251 |

*Primary Examiner*—Robert Gerstl
*Attorney, Agent, or Firm*—Joan S. Keps; Richard D. Foggio; Alan D. Lourie

[57] ABSTRACT

The invention provides 2-(3,5-disubstituted pyridylalkyl amino)-5-pyridylmethyl-4-pyrimidone derivatives which are useful as histamine H$_1$-antagonists.

15 Claims, No Drawings

HISTAMINE H₁-ANTAGONISTS

This invention relates to certain pyrimidone derivatives, compositions containing them and a method of blocking histamine H₁-receptors by administering them.

Histamine, a physiologically active compound endogenous in mammals, exerts its action by interacting with certain sites called receptors. One type of receptor is known as a histamine H₁-receptor (Ash and Schild, Brit. J. Pharmac. 1966, 27, 427) and the actions of histamine at these receptors are inhibited by drugs commonly called "antihistamines" (histamine H₁-antagonists) a common example of which is mepyramine. A second type of histamine receptor is known as the H₂-receptor (Black et al Nature 1972, 236, 385). The actions of histamine at these receptors are not inhibited by mepyramine but are inhibited by burimamide. Compounds which inhibit the actions of histamine at histamine H₂-receptors are called histamine H₂-antagonists.

U.S. Pat. No. 4,154,834 discloses compounds of general formula (I):

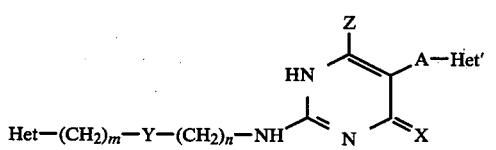

where Het is 2- or 4-imidazolyl optionally substituted by lower alkyl (preferably methy), halogen (preferably chlorine or bromine), trifluoromethyl or hydroxymethyl; 2-pyridyl optionally substituted by one or two groups (which may be the same or different) selected from lower alkyl (preferably methyl), lower alkoxy (preferably methoxy), halogen (preferably chlorine or bromine), amino and hydroxy; 2-pyridyl with a phenyl, carbocyclic or cyclic ether ring containing 2 oxygen atoms fused to it; 2-thiazolyl; 3-isothiazolyl optionally substituted by chlorine or bromine; 3-(1,2,5)-thiadiazolyl optionally substituted by chlorine or bromine, or 2-(5-amino-1,3,4-thiadiazolyl); Y is sulphur or a methylene group; m is 0, 1 or 2 and n is 2 or 3 such that their sum is 3 or 4 or when Y is methylene and Het is other than an imidazole ring, 2; Z is hydrogen or lower alkyl (preferably methyl); X is oxygen or sulphur; A is a straight or branched alkylene chain containing from 1-5 carbon atoms or —(CH₂)ₚW(CH₂)ᵩ— where W is oxygen or sulphur and p and q are such that their sum is from 1 to 4; Het' is a 5 or 6 membered heterocyclic ring selected from pyridine, pyridine-N-oxide, furan, thiophen, thiazole, oxazole, isothiazole, imidazole, pyrimidine, pyrazine, pyridazine or thiadiazole, which ring is optionally substituted by one or two (which may be the same or different) of the groups selected from lower alkyl, lower alkoxy, halo, hydroxy and amino, or Het' is a pyridine ring with a carbocyclic or cyclic ether ring containing two oxygen atoms fused to it, or Het' is a pyridine, imidazole or thiazole ring which has a benzene ring fused to it; and pharmaceutically acceptable salts thereof. These compounds are described as having combined histamine H₁- and H₂-antagonist activity.

In particular U.S. Pat. No. 4,154,834 discloses compounds of formula (I) where Het is 2-pyridyl having a substituent in position 3, Y is methylene and Het' is substituted pyridyl. It has now been found that when the 2-pyridyl group Het has a second substituent in position 5 the relative level of H₁ to H₂ activity increases. A small number of compounds, which fall within the general class of compounds of formula (I), have now been found to be useful as histamine H₁-antagonists, that is, for the treatment of diseases for example bronchial asthma, rhinitis, hayfever and allergic eczema whose symptoms are mediated through the action of histamine at H₁-receptors.

Accordingly the present invention provides compounds of formula (II):

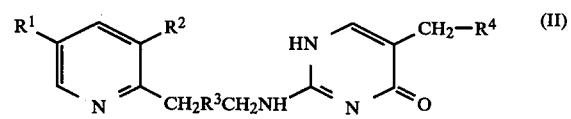

and pharmaceutically acceptable salts thereof; where $R^1$ is $C_{1-4}$ alkyl, and $R^2$ is $C_{3-4}$ alkoxy, halogen, or amino; $R^3$ is a $C_{1-3}$ alkylene group; and $R^4$ is a 3-pyridyl, N-oxo-3-pyridyl, 6-methyl-3-pyridyl, N-oxo-6-methyl-3-pyridyl, or 6-hydroxymethyl-3-pyridyl group.

Examples of $C_{1-4}$ alkyl groups for $R^1$ are methyl, ethyl, n-propyl, iso-propyl, n-butyl and t-butyl.

Preferably $R^1$ is methyl.

Examples of $C_{3-4}$ alkoxy groups for $R^2$ are n-propoxy, iso-propoxy, n-butoxy and t-butoxy.

$R^2$ can represent any one of the halogens, fluorine, chlorine, bromine or iodine.

By way of example -$R^3$- can be methylene, 1,2-ethanediyl, or 1,3-propanediyl.

Preferably $R^3$ is 1,2-ethanediyl or 1,3-propanediyl.

Preferably $R^2$ is halogen (particularly bromine) or amino. Most preferably $R^2$ is amino.

Examples of compounds within the scope of this invention are:

2-[4-(3-bromo-5-methylpyrid-2-yl)butylamino]-5-(6-methylpyrid-3-ylmethyl)-4-pyrimidone;

2-[4-(3-amino-5-methylpyrid-2-yl)butylamino]-5-(6-methylpyrid-3-ylmethyl)-4-pyrimidone;

2-[4-(3-n-propyloxy-5-methylpyrid-2-yl)butylamino]-5-(6-methylpyrid-3-ylmethyl)-4-pyrimidone;

2-[4-(3-chloro-5-methylpyrid-2-yl)butylamino]-5-(6-methylpyrid-3-ylmethyl)-4-pyrimidone;

2-[4-(3-bromo-5-methylpyrid-2-yl)butylamino]-5-(6-methyl-N-oxo-pyrid-3-ylmethyl)-4-pyrimidone;

2-[4-(3-bromo-5-methylpyrid-2-yl)butylamino]-5-(6-hydroxymethylpyrid-3-ylmethyl)-4-pyrimidone;

2-[5-(3-amino-5-methylpyrid-2-yl)pentylamino]-5-(6-methylpyrid-3-ylmethyl)-4-pyrimidone and their pharmaceutically acceptable salts.

The compounds of formula (II) are shown and described as 4-pyrimidones which exist in equilibrium with the corresponding 6-one tautomers. These compounds also exist to a lesser extent as the hydroxy tautomers, and the pyrimidine ring may also exist in the following tautomeric forms:

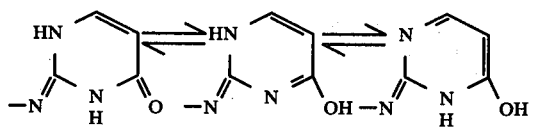

It will be understood that all these tautomeric forms are within the scope of the present invention.

The compounds of formula (II) form pharmaceutically acceptable salts with pharmaceutically acceptable salt-forming acids. Examples of these acids are hydrochloric, sulphuric, hydrobromic, phosphoric, tartaric, citric, maleic, lactic, 2-hydroxyethanesulphonic, methanesulphonic, toluene-4-sulphonic, ethanedisulphonic, ethanesulphonic and camphorsulphonic acids.

The compounds of this invention can be made by a process which comprises reacting a compound of formula (III):

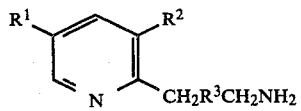

(III)

or a salt thereof, where $R^1$, $R^2$ and $R^3$ are as defined with reference to formula (II) with a compound of formula (IV):

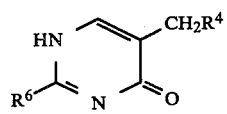

(IV)

where $R^4$ is as defined with reference to formula (II) and $R^6$ is a group displaceable with amine, thereafter optionally converting a compound of formula (II) so obtained where $R^4$ is N-oxo-6-methyl-3-pyridyl, into the corresponding compound of formula (II) where $R^4$ is 6-hydroxymethyl-3-pyridyl and optionally converting the compound of formula (II) so obtained into a pharmaceutically acceptable salt.

The compounds of formula (II) where $R^4$ is methyl N-oxo-6-methyl-3-pyridyl can be converted into the corresponding compound of formula (II) where $R^4$ is 6-hydroxymethyl-3-pyridyl by reacting them with an organic anhydride for example trifluoroacetic anhydride.

Pharmaceutically acceptable salts of compounds of formula (II) can be prepared by standard methods, for example by reacting a solution of the compound of formula (II) with a solution of the acid.

Examples of groups $R^6$ are $C_{1-4}$ alkylthio (particularly methylthio), benzylthio, chlorine, bromine and nitroamino. Preferably $R^6$ is nitroamino.

The reaction can be carried out at an elevated temperature in the absence of a solvent, for example at from 80° to 170°, preferably from 120° to 140°, or in a solvent at an elevated temperature, for example at the reflux temperature of the reaction mixture. The choice of solvent is affected by solubility characteristics of the reactants and the nature of $R^6$. Preferably the solvent is pyridine, a picoline or mixture of picolines, a $C_{1-4}$ alkanol, preferably ethanol or 1-propanol, a $C_{1-4}$ alkanol, 1,2-ethanediol, a ketone, for example acetone or 2-butanone, a high boiling alkoxyaryl ether for example anisole, or a polar aprotic solvent, for example dimethylformamide, dimethylacetamide, dimethylsulphoxide, hexamethylphosphoramide, sulpholane, acetonitrile or nitromethane.

Compounds of formula (III):

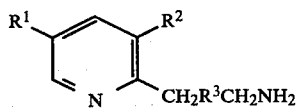

(III)

where $R^1$, $R^2$ and $R^3$ are as defined with reference to formula (II) can be prepared by reduction of the corresponding cyano compound of formula (V):

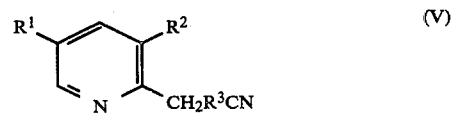

(V)

where $R^1$, $R^2$ and $R^3$ are as defined with reference to formula (III) with a reducing agent which reduces cyano to amino without reducing the groups $R^1$ and $R^2$ in a reaction medium which is inert to the reagents and product. For example the reducing agent can be lithium aluminium hydride or diborane. The reaction medium can be a dialkyl ether for example diethyl ether or a cyclic ether for example tetrahydrofuran or dioxan. Where the reducing agent is lithium aluminum hydride or diborane it will be appreciated that the reaction medium is anhydrous.

Compounds of formula (III) where $R^2$ is halogen can also be prepared from the corresponding compound of formula (III) where $R^2$ is amino. The amino group is converted into halogen by the Sandmeyer reaction, that is by diazotisation of the amino group $R^2$ and displacing the diazo group with halogen.

Compounds of formula (V) where $R^2$ is $C_{3-4}$ alkoxy can also be prepared from the corresponding compound of formula (V) where $R^2$ is amino by reaction with nitrous acid and thereafter with an alkylating agent.

Compounds of formula (V) where $R^2$ is amino can also be prepared by reducing the corresponding compound of formula (Va):

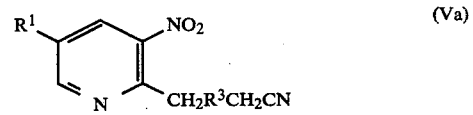

(Va)

The reduction can be carried out by hydrogenation with stannous chloride.

Cyano compounds of formula (V) and (Va) can be prepared by reacting a disubstituted chloropyridine of formula (VI):

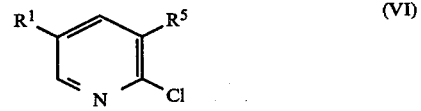

(VI)

where $R^1$ is as previously defined and $R^5$ is nitro or a group $R^2$ as previously defined with a malonic acid diester derivative of formula (VII):

(VII)

where $R^3$ is as previously defined and R are ester forming groups in the presence of a strong base in an inert reaction medium and thereafter de-esterifying and decarboxylating the product.

In particular the groups R can be ethyl.

In particular the strong base can be sodium hydride.

The reaction medium is one which is substantially inert to the reagents and product. In particular the medium can be dry tetrahydrofuran.

The compound of formula (IV):

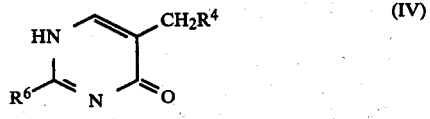

are known or can be made by analogy with known processes as disclosed in for example U.S. Pat. No. 4,154,834 and European Patent Specification No. 17,679.

Compounds of formula (II) can also be prepared by reacting a guanidine of formula (XI):

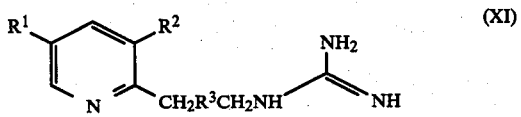

where $R^1$, $R^2$ and $R^3$ are as defined with reference to formula (II) with a compound of formula (XII):

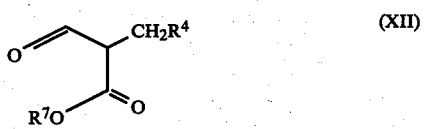

where $R^4$ is as defined with reference to formula (II) and $R^7$ is $C_{1-4}$ alkyl (particularly ethyl) benzyl or phenyl.

The reaction can be carried out by heating the guanidine of formula (XII) with the compound of formula (XIII) optionally in a solvent for example an alcohol corresponding to the ester function in the compound of formula (XIII) that is $R^7OH$, at an elevated temperature, preferably in the presence of a base in particular the sodium alkoxide $NaOR^7$ corresponding to the ester function of the compound of formula (XII).

The guanidines of formula (XII) can be prepared by reacting an amine of formula (III) with a compound of formula (XIII):

where $R^8$ is a leaving group for example methylthio or 3,5-dimethylpyrazolyl.

The histamine $H_1$-antagonist activity of the compounds of formula (II) can be demonstrated in vitro in the guinea pig ileum test. In this test an isolated portion of the guinea pig ileum is secured under tension (500 mg) between an anchorage and a transducer in a 10 ml tissue bath and immersed in magnesium free Tyrode solution with constant aeration at a temperature of 30° C. The output from the transducer is amplified. The amplified output is in turn fed to a flat bed recorder. Measured amounts of histamine are added to the tissue bath so that the histamine concentration increases step-wise until the force of the contraction reaches a maximum. The tissue bath is washed out and filled with fresh magnesium free Tyrode solution containing compound under test. The solution is left in contact with the tissue for 8 min. and measured amounts of histamine are added again until a maximum contraction is recorded. The assay is repeated with increasing concentrations of test compound and the dose of histamine giving 50% of maximum contraction is noted. A dose ratio (DR) was calculated by comparing the concentrations of histamine required to produce 50% maximum response in the absence and in the presence of the antagonist. A plot of Log DR-1 against LOG D (the concentration of compound under test) is made and the point of intersection with the Log (DR-1) ordinate is taken as the measure of the activity ($pA_2$ value). The compounds of Example 1-4, 6 and 7 have $pA_2$ values of 8.0 or above.

The histamine $H_2$-antagonist activity of the compounds of formula (II) can be demonstrated in vitro in the guinea pig atrium test. In this test a spontaneously beating isolated portion of the guinea pig right atrium is secured under tension (300 mg) between an anchorage and a transducer in a 15 ml tissue bath and immersed in McEwens solution with constant aeration at a temperature of 37° C. The output from the transducer is amplified. Output is in turn fed to a flat bed recorder. Measured amounts of histamine are added to the tissue bath so that the histamine concentration increases step-wise until the rate of beating reaches a maximum. The tissue bath is washed out and filled with fresh McEwens solution containing compound under test. The solution is left in contact with the tissue for 60 min. and measured amounts of histamine are added again until a maximum rate is recorded. The assay is repeated with increasing concentrations of test compound and the dose of histamine giving 50% of maximum rate is noted. A dose ratio (DR) was calculated by comparing the concentrations of histamine required to produce 50% maximum response in the absence and in the presence of the antagonist. A plot of Log DR-1 against LOG D (the concentration of compound under test) is made and the point of intersection with the Log (DR-1) ordinate is taken as the measure of the activity ($pA_2$ value). The compounds of Example 1-4, 6 and 7 have $pA_2$ values of less than 7.5.

The activity of compounds of formula (II) as histamine $H_1$-antagonists can be demonstrated in vivo by the inhibition of histamine induced bronchoconstriction. Guinea pigs of either sex are anaesthetised by intraperitoneal injection of sodium pentobarbitone, 90 mg/kg. The trachea is cannulated. The animal is respired artificially with a fixed volume of air just adequate to inflate the lungs. The pressure needed to inflate the lungs is monitored from the respiratory system using a low pressure transducer. Intravenous injection of histamine causes dose-dependent increases in the pressure to inflate the lungs reflecting the bronchoconstrictor action of histamine. Responses to histamine can be antagonised using histamine $H_1$-receptor antagonists.

Dose-response curves to histamine are established at 20, 40, 80, 160 and 320 nmols/kg. Antagonists are then administered by intravenous injection and 5 minutes later a new histamine dose-response curve is established increasing the doses of histamine as necessary. The effect of the antagonist can be quantified by the displacement, to the right, of the histamine dose-response curve, expressed as a dose-ratio. A series of doses of antagonists may be given to each animal allowing calculation of dose-ratios for each dose of antagonist. The compounds of the Examples hereafter cause displacement of histamine dose-response curves with a dose-ratio of 10 at doses of less than 0.8 micromole kg$^{-1}$ i.v.

The activity of the compounds of formula (II) as histamine $H_2$-antagonists can be demonstrated in vivo by the inhibition of histamine-stimulated secretion of gastric acid from the lumen-perfused stomachs of rats anaesthetised with urethane. This procedure is referred to in Ash and Schild, Brit. J. Pharmac. Chemother., 27, 247 (1966). The compounds of the Examples hereafter cause 50% inhibition of maximal acid secretion at doses of 0.1 to 20 micromole kg$^{-1}$ i.v.

In order to use the compounds of the invention as histamine $H_1$-antagonists, they can be formulated as pharmaceutical compositions in accordance with standard pharmaceutical procedure.

The invention also includes pharmaceutical compositions comprising a compound of formula (II) or a pharmaceutically acceptable salt thereof and a pharmaceutically acceptable carrier.

Compounds of formula (II) and their pharmaceutically acceptable salts can be administered topically or systemically.

Topical formulations for administration to the skin include lotions and creams. Topical formulations for administration to the respiratory tract include solutions for application via a nebulizer or as an aerosol, or a microfine insufflatable powder. The active ingredient in an insufflatable powder has a small particle size i.e. less than 50 microns and preferably less than 10 microns. The active material is co-presented with a solid carrier for example lactose which has a particle size of less than 50 microns.

Systemic administration can be achieved by rectal, oral or parenteral administration. A typical suppository formulation comprises the active compound with a binding agent and/or lubricating agent for example gelatine or cocoa butter or other low melting vegetable waxes or fats. Typical parenteral compositions consist of a solution or suspension of the active material in a sterile aqueous carrier of parenterally acceptable oil.

Compounds of formula (II) which are active when given orally can be formulated as syrups, tablets, capsules and lozenges. A syrup formulation generally consists of a suspension or solution of the compound in a liquid carrier for example ethanol, glycerine or water with a flavouring or colouring agent. Where the composition is in the form of a capsule, the solid in granular form optionally with a binding agent is encased in a gelatin shell. Where the composition is in the form of a tablet, any suitable pharmaceutical carrier routinely used for preparing solid formulations can be used. Examples of such carriers include magnesium stearate, starch, lactose, glucose, sucrose, and cellulose. Preferably the composition is in unit dose form for example a tablet, capsule or metered aerosol so that the patient may administer to himself a single dose.

Where appropriate, small amounts of bronchodilators and anti-asthmatics for example sympathomimetic amines particularly isoprenaline, isoetharine, salbutamol, phenylephrine and ephedrine; xanthine derivatives particularly theophylline and aminophylline; and corticosteroids particularly prednisolone and adrenal stimulants particularly ACTH can be included.

Each dosage unit for oral administration contains preferably from 1 to 200 mg of a compound of formula (II) or a pharmaceutically acceptable salt thereof calculated as the free base.

The invention also provides a method of blocking histamine $H_1$-receptors which comprises administering to a subject an effective amount to block said receptors of a compound of formula (II) or a pharmaceutically acceptable salt thereof.

The compounds of formula (II) and their pharmaceutically acceptable salts will normally be administered to a subject in a pharmaceutical composition as described above, for the treatment of rhinitis, hayfever, bronchial asthma or allergic eczema. An adult subject will receive an oral dose of between 15 mg and 400 mg and preferably between 15 mg and 200 mg or an intravenous, subcutaneous or intramuscular dose of between 1 mg and 50 mg, and preferably between 1 mg and 10 mg of a compound of formula (II) or a pharmaceutically acceptable salt thereof calculated as the free base, the composition being administered 1 to 4 times per day.

The following Examples illustrate the invention.

EXAMPLE 1

(a) 2-(2-Cyanoethyl)malonic acid diethylester (40 g) was reacted with sodium hydride (4.4 gm) in tetrahydrofuran at 20° C. 2-Chloro-5-methyl-3-nitro-pyridine (35 g) was added and the internal temperature was raised to 100° C. (some tetrahydrofuran distilled off) over 4.25 hrs. The reaction mixture was partitioned between chloroform and water and treated with charcoal. Vacuum distillation of the chloroform extract and then chromatography (CHCl$_3$, silica column) of the distillation residues gave 4-(5-methyl-3-nitropyrid-2-yl)-4,4-bis (carbethoxy)-butyronitrile (24.5 g) as a yellow solid m.p. 48°–49° C.

(b) The product from Example 1(a) (13.9 g) was dissolved in a mixture of ethanol (568 ml) and sodium hydroxide solution (160 ml, molar) and after having been left to stand for 4.5 days, the pH was lowered to 1.5 by addition of hydrochloric acid. The reaction mixture was heated at 50° C. for 45 minutes, neutralised and the ethanol was removed in vacuo. The product was extracted with chloroform to leave 6.7 gm of an orange solid, which was dissolved in ether and treated with charcoal to give 3-nitro-2-(3-cyanopropyl)-5-methylpyridine (6.45 g) m.p. 53°–55° C.

$C_{10}H_{11}N_3O_2$: Requires: C, 58.52; H, 5.40; N, 20.47; Found: C, 58.41; H, 5.54; N, 20.28;

(c) The product of Example 1(b) (11.07 g) was hydrogenated in ethanol with palladium on charcoal (10%) at 140 kPa for 2.5 hours. The filtered solution was concentrated to dryness, the residue was triturated with ether to give 3-amino-2(3-cyanopropyl)-5-methylpyridine (9 g) m.p. 84°–87° C.

(d) 3-Amino-2-(3-cyanopropyl)-5-methylpyridine (2.0 g) was reduced with lithium aluminium hydride (1.3 gm) in a mixture of tetrahydrofuran (110 ml) and diethyl ether (40 ml) over 3.75 hrs, to give an amber oil (2.39 g) which was partitioned between chloroform and water, the required 3-amino-2-(4-aminobutyl)-5-methylpyridine (2.7 g) was obtained from the evaporation of the chloroform extracts obtained at pH 12 and 14, as an oil which crystallised slowly.

N.M.R. (CDCl$_3$): assignment, δ (p.p.m.), multiplicity; $CH_2CH_2CH_2NH_2$, 1.4–2.0, m; 5-methylpyridyl, 2.21, s; $\underline{CH_2(CH_2)_2CH_2}$ $NH_2$, 2.6–2.9, m; 3-aminopyridyl, ca 3.6, broad resonance; 4+6 pyridyl protons, 6.75+7.8, m;

(e) The product of Example 1(d) (0.5 g) in hydrobromic acid (48%) was reacted with cuprous bromide and copper bronze. A solution of sodium nitrite in water was added at 5° to 8° C. over 45 min., the reaction mixture was allowed to stir at 5° to 8° C. for a further hour and than at room temperature for 3.5 hours. The reaction mixture was diluted with water, and hydrogen sulphide gas was passed, while the pH was progressively raised to 11 by addition of sodium hydroxide solution. The precipitated copper salts were filtered off at intervals during the above procedure. The product was then extracted at pH 11 with chloroform to give 3-bromo-2-(4-aminobutyl)-5-methylpyridine (0.5 g) as a brown oil.

N.M.R. (CDCl$_3$) assignment, δ(p.p.m.), multiplicity; CH$_2$(C$\underline{H}_2$)$_2$CH$_2$NH$_2$+NH$_2$, 1.5–1.9+1.81, m+s; 5-methylpyridyl, 2.30, s; —C$\underline{H}_2$(CH$_2$)$_2$C$\underline{H}_2$NH$_2$, 2.6–3.1, m; 4+6 pyridylprotons, 7.64+8.29, m×2;

(f) The product of Example 1(e) (0.48 g) and 2-nitroamino-5-(6-methylpyrid-3-ylmethyl)-4-pyrimidone (0.65 g) were refluxed in pyridine for 9.5 hours.

The pyridine was removed in vacuo and the residue was re-evaporated with n-propanol, triturated with chloroform, filtered and the solution was chromtographed on silica in chloroform methanol (10:1) to give 2-[4-(3-bromo-5-methylpyrid-2-yl)-butylamino]-5-(6-methylpyrid-3-ylmethyl)-4-pyrimidone (0.52 g) m.p. 148.5°–151° C.

C$_{21}$H$_{24}$Br N$_5$O: Requires: C, 57.01; H, 5.46; N, 15.83; Br, 18.06; Found: C, 56.98; H, 5.49; N, 15.77; Br, 18.31;

EXAMPLE 2

Reaction of 3-Amino-2-(4-aminobutyl)-5-methylpyridine, the product of Example 1(d) (0.61 g), with 2-nitroamino-5-(6-methylpyrid-3-ylmethyl)-4-pyrimidone (0.87 g) under conditions analogous to those in Example 1(f) gave 2-[4-(3-amino-5-methylpyrid-2-yl)butylamino]-5-(6-methylpyrid-3-ylmethyl)-4-pyrimidone (0.69 g) m.p. 86°–89° C. resolidifies and remelts at 171°–172° C.

C$_{21}$H$_{26}$N$_6$O 1.42 H$_2$O: Requires: C, 62.41; H, 7.10; N, 20.80; Found: C, 62.32; H, 6.78; N, 20.70; (Weight loss 40°–90° C.=6.35%=1.42 H$_2$O).

EXAMPLE 3

(a) A solution of 3-amino-2-(3-cyanopropyl)-5-methylpyridine [from Example 1(c)] (1 g) in diluted sulphuric acid (0.78 ml conc. and 6.5 ml water) was reacted with sodium nitrite (0.59 g in 3 ml water) between 6°–10° C. The pH was brought to 6.5 with sodium hydroxide and the product was extracted with chloroform, chromatographed on silica in chloroform-methanol giving 3-hydroxy-2-(3-cyanopropyl)-5-methylpyridine (0.51 g) m.p. 132.5° C.

(b) A solution of 3-hydroxy-2-(3-cyanopropyl)-5-methylpyridine from Example 3(a) (1.5 g), in dimethyl sulphoxide (11 ml) was first treated with sodium hydride (0.2 g) and then with n-propyl iodide in dimethyl sulphoxide (3 ml) at 17°–20° C. After stirring for four hours at room temperature, the solvent was removed in vacuo and the residue partitioned between chloroform and water, the chloroform extract was evaporated to dryness to give 3-n-propyloxy-2-(3-cyanopropyl)-5-methylpyridine (1.79 g) N.M.R. (CDCl$_3$), assignment, δ(p.p.m.), multiplicity; O(CH$_2$)$_2$CH$_3$, 1.07; t; OCH$_2$C$\underline{H}_2$CH$_3$, 1.86; m; C$\underline{H}_2$CH$_2$CN, 2.12, m; C$\underline{H}_2$CN, 2.40, m; 5-CH$_3$, 2.30, s; C$\underline{H}_2$(CH$_2$)$_2$CN, 3.94, m; OC$\underline{H}_2$, 3.91, t; 4-H pyridyl, 6.96, m; 6-H pyridyl, 7.91, m;

(c) The product from Example 3(b) (1.64 g) was reduced with lithium aluminium hydride (1.01 g) in diethyl ether (50 ml) and tetrahydrofuran (60 ml) over 5.5 hours to give 3-n-propyloxy-2-(4-aminobutyl)-5-methylpyridine (1.23 g) as an oil. N.M.R. (CDCl$_3$) assignment, δ(p.p.m.), multiplicity; O(CH$_2$)$_2$CH$_3$ 1.07 t; NH$_2$, 1.48, broad s; OCH$_2$C$\underline{H}_2$CH$_3$+CH$_2$(CH$_2$)$_2$CH$_2$NH$_2$, 1.4–2.0, m; 5CH$_3$, 2.28, s; C$\underline{H}_2$(CH$_2$)$_2$C$\underline{H}_2$NH$_2$, 2.6–2.9, m; OC$\underline{H}_2$, 3.9, t; 4H+6H pyridyl, 6.89+7.9, m×2;

(d) Reaction of the product from Example 3(b) (0.6 g) with 2-nitroamino-5-(6-methylpyrid-3-ylmethyl)-4-pyrimidone (0.78 g) under conditions analogous to those described in Example 1(f) gave 2-[4-(3-n-propyloxy-5-methylpyrid-2-yl)-butylamino]-5-(6-methylpyrid-3-ylmethyl)-4-pyrimidone (0.280 g) m.p. 81°–85° C.

C$_{24}$H$_{31}$N$_5$O$_2$ 1.5 H$_2$O: Requires: C, 64.28; H, 7.62; N, 15.61; Found: C, 64.14; H, 7.41; N, 15.38; (Loss of weight 40°–140° C.=6%=1.5 H$_2$O).

EXAMPLE 4

(a) Reaction of 3-amino-2-(4-aminobutyl)-5-methylpyridine from Example 1(d) (0.5 g) with sodium nitrite, cuprous chloride, copper bronze and hydrochloric acid under conditions analogous to those of Example 1(e) gave 3-chloro-2-(4-aminobutyl)-5-methylpyridine (0.43 g) as an oil. N.M.R. (CDCl$_3$) assignment δ(p.p.m.), multiplicity; NH$_2$, 1.56, s; CH$_2$(C$\underline{H}_2$)$_2$CH$_2$NH$_2$, 1.4–1.9, m; 5—CH$_3$, 2.29, s; —C$\underline{H}_2$NH$_2$, 2.74; m; —C$\underline{H}_2$(CH$_2$)$_3$NH$_2$, 2.91, m; 4H+6H pyridyl protons, 7.45+8.24, m×2;

(b) Reaction of the product from Example 4(a) (0.4 g) with 2-nitroamino-5-(6-methylpyrid-3-ylmethyl)-4-pyrimidone (0.63 g) under conditions analogous to those in Example 1(f) gave 2-[4-(3-chloro-5-methylpyrid-2-yl)butylamino]-5-(6-methylpyrid-3-ylmethyl)-4-pyrimidone (0.27 g) m.p. 140°–142° C.

C$_{21}$H$_{24}$Cl N$_5$O 1.4 H$_2$O: Requires: C, 59.58; H, 6.38; N, 16.54; Cl, 8.37; Found: C, 59.79; H, 6.12; N, 16.58; Cl, 8.14; (loss of weight 40°–70° C.=6%=1.4 H$_2$O).

EXAMPLE 5

Reaction of the product from Example 1(e) (0.60 g) with 2-nitroamino-5-(N-oxo-6-methylpyrid-3-ylmethyl)-4-pyrimidon (0.82 g) under conditions analogous to those described in Example 1(f) gave 2-[4-(3-bromo-5-methylpyrid-2-yl)-butylamino]-5-(6-methyl-N-oxopyrid-3-ylmethyl)-4-pyrimidone (0.71 g), m.p. 175°–182° C.

EXAMPLE 6

Reaction of the product from Example 5 (0.36 g) in dichloromethane (3 ml) with trifluoroacetic anhydride, for two days, followed by removal of the solvent in vacuo, dissolution of the residue in chloroform, washing of the chloroform solution with 10% sodium bicarbonate solution, and concentrating the chloroform solution to dryness gave an oil 0.43 gm. This oil was chromatographed on silica in methanol-chloroform and recrystallised from acetonitrile-water giving 2-[4-(3-bromo-5-methylpyrid-2-yl)-butylamino]-5-(6-hydroxymethylpyrid-3-ylmethyl)-4-pyrimidone, (0.24 g) m.p. 150°–152° C.

C$_{21}$H$_{24}$ Br N$_5$O$_2$ 1.2 H$_2$O: Requires: C, 52.54; H, 5.54; Br, 16.65; N, 14.59; Found: C, 52.69; H, 5.41; Br, 15.90;N, 14.46; (loss of weight 40°–150° C.=6%=1.2 H$_2$O)

EXAMPLE 7

(a) 2-Chloro-5-methyl-3-nitro-pyridine (20 g) was reacted with 2-(3-cyanopropyl)malonic acid diethyl ester under conditions analogous to those in Example 1(a). The reaction mixture was partitioned between water and chloroform, the chloroform extract was dried, treated with charcoal and filtered through a silica bed and then evaporated to dryness to give 2-[4-cyano-1,1-dicarbethoxybutyl]-3-nitro-5-methylpyridine (18.3 g) as a yellow oil. N.M.R. (CDCl$_3$) assignment, δ(p.p.m.), multiplicity; CO$_2$C$\underline{H_2}$CH$_3$×2, 1.2, t; —CH$_2$C$\underline{H_2}$CH$_2$CN, 1.3-2.0, m; —C$\underline{H_2}$CN, 2.37, m; 5-methylpyridyl, 2.49, s; CO$_2$CH$_2$C$\underline{H_3}$×2, 4.19, q; 4-pyridyl proton 8.17, m; 6-pyridyl proton, 8.57, m;

(b) The product from Example 7(a) (5 g) was dissolved in a mixture of ethanol (206 ml) and sodium hydroxide solution (58 ml, molar) and left in the dark for 6 days. The pH was lowered to 1.5 by the addition of hydrochloric acid, the reaction mixture was heated in a water bath at 50° C. for 75 mins, pH raised to 7, and ethanol was distilled off. The product was extracted with chloroform to give an oil (4.4 g). This oil was extracted with dilute hydrochloric acid. (16 ml of 1.5 N) re-extracted with more dilute hydrochloric acid and the combined acid extracts were then extracted with chloroform to give 3-nitro-2-(3-cyanobutyl)-5-methylpyridine (1.61 g) as a yellow oil. N.M.R. (CDCl$_3$) assignment, δ(p.p.m.), multiplicity; —CH$_2$CH$_2$CH$_2$CN, 1.5-2.2, m; 5—CH$_3$, 2.43, s; C$\underline{H_2}$CN, 2.43, m; C$\underline{H_2}$(CH$_2$)$_3$CN, 3.11, m; 4—H pyridine, 8.02, m; 6—H pyridine, 8.58, m;

(c) Hydrogenation of the product of Example 7(b) under conditions analogous to those of Example 1(c) gave 3-amino-2-(3-cyanobutyl)-5-methylpyridine (1.21 g) m.p. 112°-114° C.

(d) 3-Amino-2-(3-cyanobutyl)-5-methylpyridine (1.13 g) was reduced with lithium aluminium hydride (0.8 g) in a mixture of tetrahydrofuran (100 ml) and diethyl ether (10 ml) over 3.5 hours. The crude product was obtained as a yellow oil (1.23 g) which was chromatographed in ammonia-ethyl acetate-ethanol on silica to give 3-amino-2-(5-aminopentyl)-5-methylpyridine (0.41 g) as a yellow waxy solid. N.M.R. (CDCl$_3$) assignment, (p.p.m.), multiplicity; CH$_2$(C$\underline{H_2}$)$_3$CH$_2$NH$_2$, ca 1.5, m; CH$_2$NH$_2$, 1.73, broad s; 5—CH$_3$, 2.22, s; C$\underline{H_2}$(CH$_2$)$_3$CH$_2$NH$_2$, 2.5-2.9, m; 3—NH$_2$, ca. 3.6, broad resonance; 4—H pyridyl, 6.76, m; 6—H pyridyl, 7.81, m.

(e) Reaction of the product of Example 7(d) (0.32 g) with 2-nitroamino-5-(6-methylpyrid-3-ylmethyl)-4-pyrimidone (0.56 g) under conditions analogous to those in Example 1(f) gave 2-[5-(3-amino-5-methylpyrid-2-yl)-pentylamino]-5-(6-methylpyrid-3-ylmethyl)-4-pyrimidone (0.36 gm) m.p. 161°-163° C.

C$_{22}$H$_{28}$N$_6$O 2.8H$_2$O: Requires: C, 59.67; H, 7.62; N, 18.98. Found: C, 59.71; H, 7.65; N, 18.92 (weight loss 50°-90° C. = 11.36% = 2.8H$_2$O)

EXAMPLE 8

A pharmaceutical composition for oral administration is prepared containing

| | | % by weight |
|---|---|---|
| A | 2-[4-(3-bromo-5-methylpyrid-2-yl)-butylamino]-5-(6-methylpyrid-3-ylmethyl)-4-pyrimidone | 55 |
| | Dibasic calcium phosphate dihydrate | 20 |
| | Approved coloring agent | 0.5 |
| | Polyvinylpyrrolidone | 4.0 |
| | Microcrystalline Cellulose | 8.0 |
| B | Maize Starch | 8.0 |
| | Sodium glycollate | 4.0 |
| | Magnesium Stearate | 0.5 | by mixing together the ingredients A (substituting lactose or microcrystalline cellose for dibasic calcium phosphate dihydrate if desired), adding a concentrated solution of polyvinylpyrrolidone and granulating, drying and screening the dried granules; adding the ingredients B to the dried granules and compressing the mixture into tablets containing 5 mg, 25 mg or 50 mg of the free base.

Other compounds of the invention, for example those specifically described in Examples 2 to 7 can be formulated into pharmaceutical compositions by a similar procedure.

EXAMPLE 9

A pharmaceutical composition for injectable administration is prepared by forming a solution of 2-[4-(3-bromo-5-methyl-pyrid-2-yl)-butylamino]-5-(6-methyl-pyrid-3-ylmethyl)-4-pyrimidone hydrochloride salt in sterile water to give a 1 to 5% w/w solution. The solution is clarified by filtration and filled into vials which are sealed and sterilised. A suitable vial contains 2 ml of the solution.

I claim:

1. A compound of formula (II):

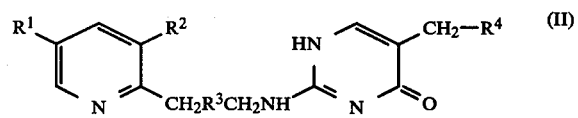

or a pharmaceutically acceptable salt thereof; where R$^1$ is C$_{1-4}$ alkyl, and R$^2$ is C$_{3-4}$ alkoxy, halogen, or amino; R$^3$ is a C$_{1-3}$ alkylene group; and R$^4$ is a 3-pyridyl, N-oxo-3-pyridyl, 6-methyl-3-pyridyl, N-oxo-6-methyl-3-pyridyl or 6-hydroxymethyl-3-pyridyl group.

2. A compound according to claim 1 where R$^1$ is methyl.

3. A compound according to claim 1 where R$^2$ is amino or halogen.

4. A compound according to claim 3 where R$^2$ is amino.

5. A compound according to claim 1 where R$^4$ is 6-methyl-pyrid-3-yl.

6. A compound according to claim 1 which is 2-[4-(3-bromo-5-methylpyrid-2-yl)butylamino]-5-(6-methylpyrid-3-ylmethyl)-4-pyrimidone or a pharmaceutically acceptable salt thereof.

7. A compound according to claim 1 which is 2-[4-(3-amino-5-methylpyrid-2-yl)butylamino]-5-(6-methylpyrid-3-ylmethyl)-4-pyrimidone or a pharmaceutically acceptable salt thereof.

8. A compound according to claim 1 which is 2-[4-(3-n-propyloxy-5-methylpyrid-2-yl)butylamino]-5-(6-methylpyrid-3-ylmethyl)-4-pyrimidone or a pharmaceutically acceptable salt thereof.

9. A compound according to claim 1 which is 2-[4-(3-chloro-5-methylpyrid-2-yl)butylamino]-5-(6-methyl pyrid-3-ylmethyl)-4-pyrimidone or a pharmaceutically acceptable salt thereof.

10. A compound according to claim 1 which is 2-[4-(3-bromo-5-methylpyrid-2-yl)butylamino]-5-(6-methyl- N-oxo-pyrid-3-ylmethyl)-4-pyrimidone or a pharmaceutically acceptable salt thereof.

11. A compound according to claim 1 which is 2-[4-(3-bromo-5-methylpyrid-2-yl)butylamino]-5-(6-hydroxymethylpyrid-3-ylmethyl)-4-pyrimidone or a pharmaceutically acceptable salt thereof.

12. A compound according to claim 1 which is 2-[5-(3-amino-5-methylpyrid-2-yl)pentylamino]-5-(6-methylpyrid-3-ylmethyl)-4-pyrimidone or a pharmaceutically acceptable salt thereof.

13. A hydrochloride salt of a compound of formula (II) according to claim 1.

14. A pharmaceutical composition having histamine $H_1$-antagonist activity comprising an effective amount of a compound according to claim 1 and a pharmaceutically acceptable carrier.

15. A method of blocking histamine $H_1$-receptors which comprises administering to a subject an effective amount to block said receptors of a compound according to claim 1.

* * * * *